(12) United States Patent
Carlton et al.

(10) Patent No.: US 8,812,123 B2
(45) Date of Patent: Aug. 19, 2014

(54) PATIENT PROGRAMMER WITH INPUT AND SENSING CAPABILITIES

(75) Inventors: Keith Carlton, Cleveland, OH (US); Scott Kokones, Cleveland, OH (US)

(73) Assignee: Intelect Medical, Inc., Natick, MA (US)

( * ) Notice: Subject to any disclaimer, the term of this patent is extended or adjusted under 35 U.S.C. 154(b) by 1355 days.

(21) Appl. No.: 11/873,842

(22) Filed: Oct. 17, 2007

(65) Prior Publication Data

US 2009/0105787 A1     Apr. 23, 2009

(51) Int. Cl.
*A61N 1/36*     (2006.01)
*A61N 1/372*    (2006.01)

(52) U.S. Cl.
CPC .................... *A61N 1/37235* (2013.01)
USPC ............................... 607/59; 607/62

(58) Field of Classification Search
CPC .................................. A61N 1/37235
USPC ........................ 607/2, 6, 18, 32, 45, 59–60, 62
See application file for complete search history.

(56) References Cited

U.S. PATENT DOCUMENTS

| | | | |
|---|---|---|---|
| 5,749,904 A | 5/1998 | Gliner et al. | |
| 6,442,432 B2 | 8/2002 | Lee | |
| 6,507,759 B1 | 1/2003 | Prutchi et al. | |
| 6,609,031 B1 | 8/2003 | Law et al. | |
| 6,631,297 B1 | 10/2003 | Mo | |
| 6,654,642 B2 | 11/2003 | North et al. | |
| 6,662,053 B2 | 12/2003 | Borkan | |
| 6,684,106 B2 | 1/2004 | Herbst | |
| 6,690,974 B2 | 2/2004 | Archer et al. | |
| 6,748,276 B1 | 6/2004 | Daignault, Jr. et al. | |
| 6,937,891 B2 | 8/2005 | Leinders et al. | |
| 6,944,501 B1 | 9/2005 | Pless | |
| 7,127,297 B2 | 10/2006 | Law et al. | |
| 7,228,179 B2 | 6/2007 | Campen et al. | |
| 7,254,445 B2 | 8/2007 | Law et al. | |
| 7,266,412 B2 | 9/2007 | Stypulkowski | |
| 2001/0031071 A1 * | 10/2001 | Nichols et al. | 382/115 |
| 2002/0115603 A1 * | 8/2002 | Whitehouse | 514/12 |
| 2003/0171791 A1 * | 9/2003 | KenKnight et al. | 607/60 |
| 2004/0054297 A1 | 3/2004 | Wingeier et al. | |
| 2004/0059395 A1 | 3/2004 | North et al. | |
| 2004/0152957 A1 | 8/2004 | Stivoric et al. | |
| 2004/0181262 A1 * | 9/2004 | Bauhahn | 607/48 |
| 2005/0075689 A1 | 4/2005 | Toy et al. | |
| 2006/0218007 A1 | 9/2006 | Bjorner et al. | |
| 2007/0135855 A1 | 6/2007 | Foshee et al. | |
| 2007/0265664 A1 * | 11/2007 | Gerber et al. | 607/2 |

OTHER PUBLICATIONS

PCT Notification of Transmittal of the International Search Report and the Written Opinion of the International Searching Authority, or the Declaration dated Dec. 5, 2008.
EP 08838653.7—Extended European Search Report dated Oct. 26, 2010.

* cited by examiner

*Primary Examiner* — Carl H Layno
*Assistant Examiner* — Jennifer Ghand
(74) *Attorney, Agent, or Firm* — Kenyon & Kenyon LLP

(57) ABSTRACT

A patient programmer can have a progress module, wherein the progress module may obtain progress input from a patient in which the generator is implanted. The progress module may include sensors that are able to obtain progress input based on patient interactions with sensors coupled to the patient programmer. The progress module may also include an interface that poses progress-related questions to the patient and obtains responses to the questions from the patient. The patient programmer is also able to store the progress input for reporting purposes.

23 Claims, 3 Drawing Sheets

PATIENT PROGRAMMER WITH INPUT AND SENSING CAPABILITIES

BACKGROUND

1. Technical Field

This disclosure generally relates to the treatment and rehabilitation of patients having implanted medical devices. More particularly, the disclosure relates to patient programmers used with implantable neuro-stimulators.

2. Discussion

Implantable neuro-stimulators have begun to demonstrate clinical usefulness for a wide variety of conditions such as spinal cord injury, traumatic brain injury (TBI), stroke, Parkinson's disease and Parkinson's tremor. For example, deep brain stimulation (DBS) systems have been used to successfully improve motor control in Parkinson's patients by delivering electrical pulses to selected areas of the brain. While certain developments in neuro-stimulators have advanced rehabilitation and treatment in a number of areas, certain challenges remain.

For example, when a patient having an implanted device is discharged from a medical facility, the patient is often provided with a patient programmer, which gives the patient limited control over the implanted device. Indeed, early patient programmers often only provided the patient with the ability to turn the implanted device on and off. While more recent patient programmers have given patients slightly more control over the functionality of the implanted device, there still remains considerable room for improvement.

BRIEF DESCRIPTION OF THE DRAWINGS

The various advantages of the embodiments of the present invention will become apparent to one skilled in the art by reading the following specification and appended claims, and by referencing the following drawings, in which:

DETAILED DESCRIPTION

Embodiments of the present invention provide for a patient programmer having a control module, a communication interface, and a progress module. The control module may generate a control signal and the communication interface can transmit the control signal to a generator of a stimulation signal. The progress module can obtain progress input from a patient in which the generator is implanted.

In another embodiment of the invention, a deep brain stimulation (DBS) patient programmer includes a control module that generates a switching signal, wherein the switching signal instructs a generator of a brain stimulation signal to transition between an on-state and an off-state. A short range wireless interface may transmit the switching signal to the generator. The patient programmer may also include a progress module having a sensor mounted to the patient programmer to obtain a first set of progress inputs from a patient in which the generator is implanted. The progress module can also include a display or other output device that presents a plurality of questions to the patient, and an input device to receive answers to the plurality of questions from the patient. The answers can therefore define a second set of progress inputs. The progress module may further include a memory location to store the first and second sets of progress inputs, wherein the patient programmer can include a wired or wireless interface to transmit report data representing the first and second sets of progress inputs to a clinician programmer.

In yet another embodiment of the invention, a method of operating a patient programmer can provide for generating a switching signal and transmitting the switching signal from the patient programmer to a generator of a brain stimulation signal. The switching signal can instruct the generator to transition between an on-state and an off-state. The method may also provide for using a progress module of the patient programmer to obtain progress input from a patient in which the generator is implanted.

Figure 1:
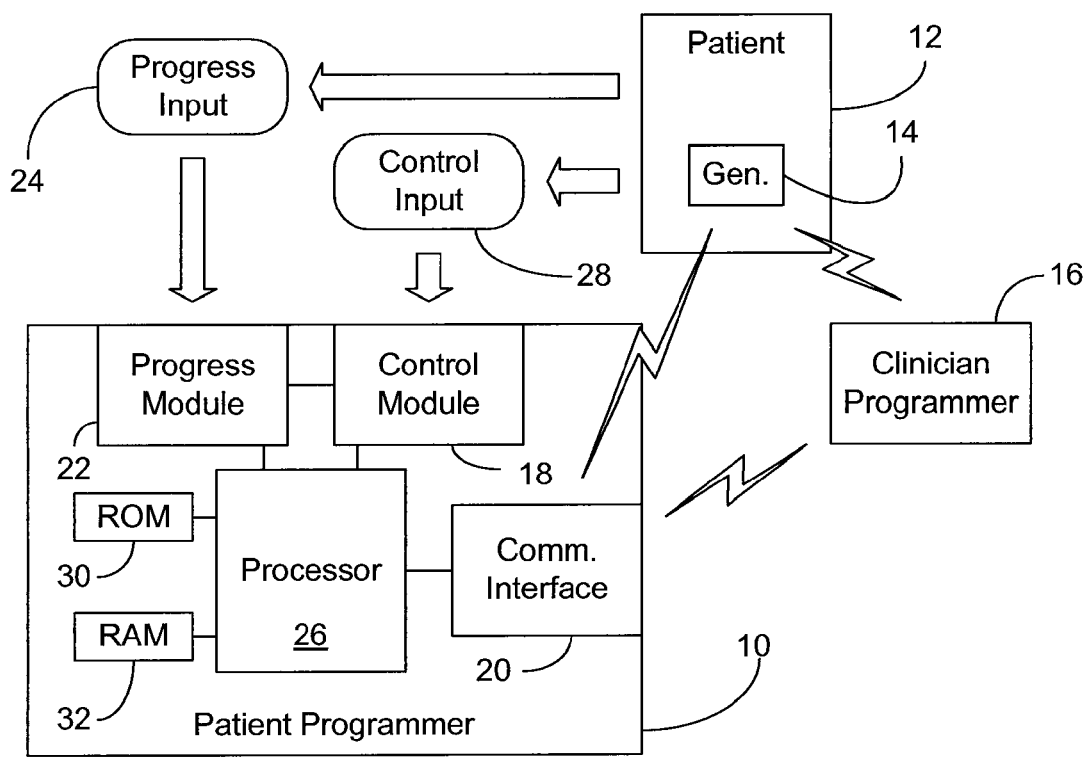
FIG. 1 is a block diagram of an example of a patient programmer according to an embodiment of the invention.

FIG. 1 shows a patient programmer 10 that can generally be used to enhance the treatment and rehabilitation of a patient 12 having an implanted medical device such as a neuro-stimulation generator 14. The generator 14 may be used to deliver electrical pulses to areas of the patient's body such as, for example, the brain, spinal cord, or other parts of the nervous system, via one or more suitable electrical leads (not shown), which may also be implanted in the patient 12. For example, the generator 14 may be implanted by placing the generator 14 in a sub-cutaneous pocket created by making a blunt dissection in the subclavicular region, wherein the generator 14 can include one or more suture holes for securing the generator 14 to the muscle facia. In addition, the corresponding electrical leads may be tunneled to the distal end of an extension (not shown), and the extension may be tunneled to the generator 14 using well-known implantation procedures.

In this regard, the generator 14 may have a wide range of non-invasively programmable parameters and stimulation modes, and can exchange parameter information, via telemetry, with a clinician programmer 16 and the patient programmer 10. Communication with the illustrated patient programmer 10 is implemented through a communication interface 20 of the patient programmer 10. The stimulation pulses delivered to each lead can be determined by a parameter called a program, wherein a program can be a specific combination of amplitude, rate and pulse width parameters acting on a specific lead electrode set. For the stimulation signals, example amplitudes might range from 0.0-20.0 mA, example pulse widths may range from 10-1000 μsec per phase, example frequencies may range from 1-1200 Hz, and the waveform shape might be square, sine, or triangle wave. Other parameter ranges and characteristics may also be used.

In one embodiment, the clinician programmer 16, which typically runs as an application on a laptop- or PC-based platform, can be used to determine which programs are to be run on the generator 14 and may display instruction prompts for the clinician and show parameter data. The clinician programmer 16 can also be used to provide stimulation parameters and patient programmer adjustment limits for multiple programs, collect measurements and diagnostic data from the generator 14 and may be used to switch the generator 14 on and off, and obtain the battery status of the generator 14, which may be powered by a hermetically sealed silver vanadium oxide cell, a lithium ion cell, or other state of the art battery chemistries. In particular, upon interrogation by the clinician programmer 16, the generator 14 might transmit via an RF link to the clinician programmer 16 for display or printing: patient progress reports received from the patient programmer 10, model and serial number identification, programmed parameters and values, generator battery status, number of patient activations (since last reset), total stimulation time (since last reset), elapsed time (since last reset) and verification of program changes. After a program entry, the clinician programmer 16 can compare stimulation signal parameters, via telemetry, with the entries made during programming.

The illustrated patient programmer 10, which may be a relatively small handheld device, has a control module 18 that generates a control signal such as a switching signal to instruct the generator 14 to transition between the on and off state based on control input 28 from the patient 12. Thus, the patient 12 can use the patient programmer 10 to power the generator 14 on and off. Other control input 28 such as selection of program parameters and stimulation modes may also be obtained from the patient 12, although it may be desirable to limit such control by the patient 12 for safety concerns. Likewise, other control signals, such as program parameter and stimulation mode selection signals, may also be generated based on the control input 28 and transmitted to the generator 14. Such control input 28 may be obtained from the patient 12 via an appropriate user interface such as a touch screen display, keypad and/or button. A processor 26 may use the communication interface 20 to transmit the switching signal to the generator 14 wirelessly, using a short range wireless interface such as a WPAN (Wireless Personal Area Network; e.g., IEEE 802.15.4) module, a Bluetooth (e.g., IEEE 802.15.1) module, a WiFi (Wireless Fidelity; e.g., IEEE 802.11) module, or an RF (Radio Frequency) module using the MICS (Medical Implant Communication Service; e.g., 47 CFR 95.601-95.673 Subpart E), for example.

The patient programmer 10 may also include a progress module 22 that can obtain progress input 24 from the patient 12. Enabling the patient to provide progress input 24 through the patient programmer 10 represents a substantial improvement over conventional approaches. For example, the patient programmer 10 is typically much more accessible to the patient 12 than other devices such as the clinician programmer 16, and the patient programmer 10 tends to be much more "personal" to the patient. Accordingly, the illustrated patient programmer 10 can collect progress input 24 more frequently (e.g., daily) and is more likely to obtain accurate results and/or truthful responses from the patient 12. In addition, while the patient programmer 10 may have substantially more functionality than traditional patient programmers, the programmer 10 can maintain a desired level of safety by limiting control input 28 to only certain features such as on/off control and predefined parameter set selection. Meanwhile, the illustrated patient programmer 10 is able to provide robust progress input 24 collection and reporting functionality that may significantly enhance patient recovery.

The progress input 24 may also be used in a closed-loop fashion by the patient programmer 10 to select and/or modify program parameters and/or stimulation modes in real-time, wherein the patient programmer 10 can generate the appropriate control signals and transmit them to the generator 14. In such a case, certain precautions such as patient authentication features can be implemented in order to better ensure patient safety. Examples of such precautions are described in greater detail below.

The progress input 24 can include measurements taken from sensors mounted on or otherwise coupled to the patient programmer 10, answers to rehabilitation related questions, and so on. The processor 26 can store the progress input 24 to a memory location in read only memory (ROM) 30, random access memory (RAM) 32, or any other suitable memory structure. The progress input 24 can also be transmitted, via the communication interface 20, to the generator 14 as report data, wherein the clinician programmer 16 may obtain the report data from the generator 14 over a long range wireless interface such as an RF telemetry module or a WiMAX (Worldwide Interoperability for Microwave Access; e.g., IEEE 802.16) module, or a short range wireless interface. The clinician programmer 16 may also obtain the report data directly from the patient programmer 10 via a short range wireless interface, wired interface such as a USB (Universal Serial Bus) connection or an Ethernet (e.g., IEEE 802.3) connection, or long range wireless interface, depending upon the circumstances. The short and long range wireless interfaces would be suited for communications that take place during office visits, whereas the long range wireless interface could permit more frequent transmissions of data between the generator 14, patient programmer 10 and the clinician programmer 16. In addition, the report data may be transmitted to a home monitor and/or Internet connection.

Figure 2:
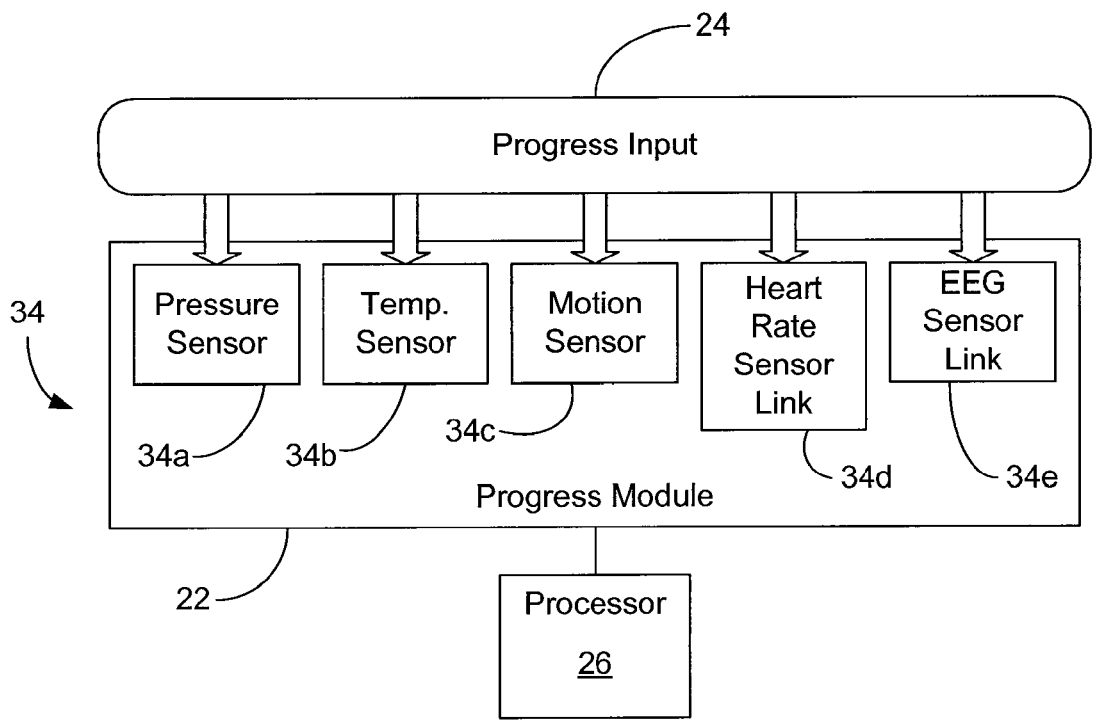
FIG. 2 is a block diagram of an example of a progress module according to an embodiment of the invention.

Turning now to FIG. 2, one example of progress input 24 being obtained from the patient's interaction with a plurality of sensors 34 (34a-34e) is shown. The illustrated sensors 34 may be mounted on the patient programmer, wired to the patient programmer or linked to the patient programmer through a wireless connection, and may be used to assess the progress of the patient. In particular, the patient could perform a task with the patient programmer, wherein the sensors 34 may take measurements associated with the task. For example, the patient could be instructed to manipulate one or more pressure sensors 34a so that the amount of pressure exerted by the patient could be measured and tracked over time to show improvement. In another task, the patient could be asked to pull on a strain gauge (not shown) in order to measure the strength of the patient. A temperature sensor 34b may be used to measure body and/or ambient temperature associated with particular tasks and a motion sensor 34c could be used for a motor skills task such as lifting the patient programmer off of a table and raising it above one's head. The motion sensor 34c may therefore track the speed and duration of the task and output this information for storage on the patient programmer and reporting purposes.

The illustrated progress module 22 also interacts with sensors external to the patient programmer to give a more complete view of the patient recovery. For example, the motion sensor 34c could interact with a sensor held by the patient during rehabilitation tasks. This interaction could indicate the distance traveled by the patient's extremity during the course of a specific rehabilitation task. Another example is that the motion sensor 34c could interact with a sensor implanted in the patient as part of the implantable therapeutic system. One possibility is that the interaction of these sensors could indicate overall movement of the patient in both body and head movement, which could be informative as to the overall rehabilitation status of the patient. Another possibility is that each of the sensors could generate independent readings, wherein the patient programmer conducts an analysis of the readings to obtain information regarding the patient's progress. The illustrated progress module 22 also includes a heart rate sensor link 34d and an EEG sensor link 34e, which can receive measurement signals from heart rate and EEG sensors coupled to the patient, respectively. Based on the progress input from the EEG sensors, for example (which could detect brain activity, sleep cycles, etc.), the patient programmer can instruct the patient to perform different tasks. Other sensors, such as chemical pH sensors, may also be used.

Figure 3A:
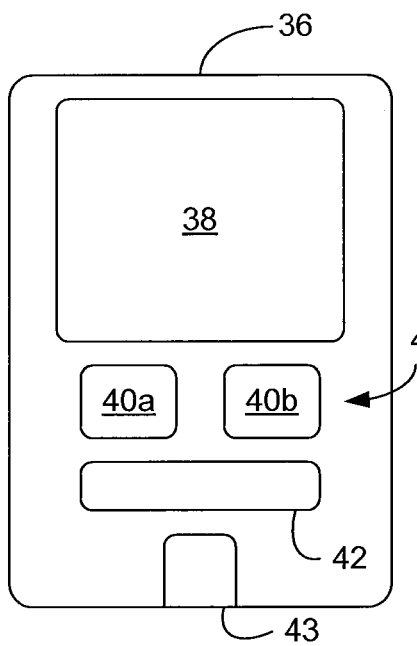
FIG. 3A is a front view of an example of a patient programmer having a pressure bar according to an embodiment of the invention.

FIG. 3A shows an external view of an example of a patient programmer 36. In particular, the patient programmer 36 may be able to obtain progress input from a patient having an implanted medical device such as a DBS neuro-stimulation generator, store the progress input, and report the progress input to another device such as the generator or a clinician programmer. In the illustrated example, the patient programmer 36 has a display 38, an input device including a plurality of buttons 40 (40a, 40b), and a pressure bar 42. The patient programmer 36 can use the display 38 and/or other output device such as a speaker to provide instructions and information to the patient. The instructions could be output periodically, such as daily, and/or in a closed-loop fashion in response to progress input already obtained from the patient. For example, the patient programmer 36 may use the display 38 to instruct the patient to press on the pressure bar for a certain amount of time, wherein the pressure bar 42 measures the amount of pressure applied by the patient. This progress input may be registered and time stamped by a processor 26 and/or progress module 22 (FIG. 1), and stored to a memory location within the patient programmer 36. Tracking such progress input over time and reporting the information back to the clinician programmer enables the medical professional to more readily ascertain the progress of the patient and the effectiveness of the underlying medical treatment. The progress input from the pressure bar 42 may also be used to select subsequent instructions to be presented to the patient. Examples of instructions include, but are not limited to, instructions to squeeze sensors on the patient programmer 36, press down on sensors on the patient programmer 36, perform range of motion exercises with the patient programmer 36 in hand, pick up and put down the patient programmer 36, and manipulate a button on the patient programmer 36 when an object on the display 38 disappears/appears as part of a reaction time test.

The display 38 may also be used to present questions to the patient that are tailored to the patient's progress, wherein the patient can provide answers to the questions via the illustrated buttons 40. Thus, the progress input may be obtained from the patient through the illustrated buttons 40 as well as the illustrated pressure bar 42. The questions could be related to the patient's perception of improvement, the patient's psychological state, objective yes/no issues, or anything else related to the patient's well-being or state of recovery. In general, questions may be related to quality of life (e.g., physical, emotional, task oriented), object recognition (e.g., display an apple, plane, basketball, etc., and have the patient choose from a multiple choice list what the object is), diary input (e.g., time/date stamp for eating, bathing, voiding), and cognitive state (e.g., IQ).

For example, Table 1 shows a plurality of Barthel Index questions, which may be presented to the patient on display 38 of the patient programmer 36.

TABLE 1

| Barthel Index Activity | Score |
|---|---|
| FEEDING | |
| 0 = unable<br>5 = needs help cutting, spreading butter, etc., or requires modified diet<br>10 = independent | |
| BATHING | |
| 0 = dependent | |

TABLE 1-continued

| Barthel Index Activity | Score |
|---|---|
| 5 = independent (or in shower) | |
| GROOMING | |
| 0 = needs to help with personal care<br>5 = independent face/hair/teeth/shaving (implements provided) | |
| DRESSING | |
| 0 = dependent<br>5 = needs help but can do about half unaided<br>10 = independent (including buttons, zips, laces, etc.) | |
| BOWELS | |
| 0 = incontinent (or needs to be given enemas)<br>5 = occasional accident<br>10 = continent | |
| BLADDER | |
| 0 = incontinent, or catheterized and unable to manage alone<br>5 = occasional accident<br>10 = continent | |
| TOILET USE | |
| 0 = dependent<br>5 = needs some help, but can do something alone<br>10 = independent (on and off, dressing, wiping) | |
| TRANSFERS (BED TO CHAIR AND BACK) | |
| 0 = unable, no sitting balance<br>5 = major help (one or two people, physical), can sit<br>10 = minor help (verbal or physical)<br>15 = independent | |
| MOBILITY (ON LEVEL SURFACES) | |
| 0 = immobile or <50 yards<br>5 = wheelchair independent, including corners, >50 yards<br>10 = walks with help of one person (verbal or physical) >50 yards<br>15 = independent (but may use any aid; for example, stick) >50 yards | |
| STAIRS | |
| 0 = unable<br>5 = needs help (verbal, physical, carrying aid)<br>10 = independent | |

Table 2 shows a plurality of Short Form 36 (SF-36) Health Survey questions, which may be presented to the patient on display 38 of the patient programmer 36.

TABLE 2

| SF-36 Health Survey Question |
|---|
| 1. In general, would you say your health is:<br>__Excellent<br>__Very Good<br>__Good<br>__Fair<br>__Poor |
| 2. Compared to one year ago, how would you rate your health in general now?<br>__Much better now than a year ago<br>__Somewhat better now than a year ago<br>__About the same as one year ago<br>__Somewhat worse now than one year ago<br>__Much worse now than one year ago<br>.<br>.<br>. |
| 11. How TRUE or FALSE is each of the following statements for you?<br>a. I seem to get sick a little easier than other people<br>__Definitely true<br>__Mostly true<br>__Don't know<br>__Mostly false<br>__Definitely false |

TABLE 2-continued

| SF-36 Health Survey Question |
| --- |
| b. I am as healthy as anybody I know |
| _Definitely true |
| _Mostly true |
| _Don't know |
| _Mostly false |
| _Definitely false |
| c. I expect my health to get worse |
| _Definitely true |
| _Mostly true |
| _Don't know |
| _Mostly false |
| _Definitely false |
| d. My health is excellent |
| _Definitely true |
| _Mostly True |
| _Don't know |
| _Mostly false |
| _Definitely false |

Table 3 shows a plurality of Stroke Specific Quality of Life Scale (SS-QOL) questions, which may be presented to the patient on the display 38 of the patient programmer 36.

TABLE 3

| SS-QOL Item | Score |
| --- | --- |
| Energy | |
| 1. I felt tired most of the time. | |
| 2. I had to stop and rest during the day. | |
| 3. I was too tired to do what I wanted to do. | |
| Family Roles | |
| 1. I didn't join in activities just for fun with my family. | |
| 2. I felt I was a burden to my family. | |
| 3. My physical condition interfered with my personal life. | |
| Language | |
| 1. Did you have trouble speaking? For example, get stuck, stutter, stammer, or slur your words? | |
| 2. Did you have trouble speaking clearly enough to use the telephone? | |
| 3. Did other people have trouble in understanding what you said? | |
| 4. Did you have trouble finding the word you wanted to say? | |
| 5. Did you have to repeat yourself so others could understand you? | |
| . | |
| . | |
| . | |
| Work Productivity | |
| 1. Did you have trouble doing daily work around the house? | |
| 2. Did you have trouble finishing jobs that you started? | |
| 3. Did you have trouble doing the work you used to do? | |

Copyright© 1997-2007—Internet Stroke Center

The patient programmer 36 may also provide instructions for tasks to be performed with other objects, wherein the patient and/or rehab technician may enter performance scores into to the patient programmer. Table 4 shows a plurality of Action Research Arm Test instructions/questions, which may be presented to the patient on the display 38 of the patient programmer 36.

TABLE 4

| Action Research Arm Test Activity | Score |
| --- | --- |
| Grasp | |
| 1. Block, wood, 10 cm cube (If score = 3, total = 18 and go to Grip) Pick up a 10 cm block | |
| 2. Block, wood, 2.5 cm cube (If score = 0, total = 0 and go to Grip) Pick up 2.5 cm block | |
| 3. Block, wood, 5 cm cube | |
| 4. Block, wood, 7.5 cm cube | |
| 5. Ball (Cricket), 7.5 cm diameter | |
| 6. Stone 10 × 2.5 × 1 cm | |
| Coefficient of reproducibility = 0.98 | |
| Coefficient of scalability = 0.94 | |
| Grip | |
| 1. Pour water from glass to glass (If score = 3, total = 12, and go to Pinch) | |
| 2. Tube 2.25 cm (If score = 0, total = 0 and go to Pinch) | |
| 3. Tube 1 × 16 cm | |
| 4. Washer (3.5 cm diameter) over bolt | |
| Coefficient of reproducibility = 0.99 | |
| Coefficient of scalability = 0.98 | |
| Pinch | |
| 1. Ball bearing, 6 mm, $3^{rd}$ finger and thumb (If score = 3, total = 18 and go to Grossmt) | |
| 2. Marble, 1.5 cm, index finger and thumb (If score = 0, total = 0 and go to Grossmt) | |
| 3. Ball bearing $2^{nd}$ finger and thumb | |
| 4. Ball bearing $1^{st}$ finger and thumb | |
| 5. Marble $3^{rd}$ finger and thumb | |
| 6. Marble $2^{nd}$ finger and thumb | |
| Coefficient of reproducibility = 0.99 | |
| Coefficient of scalability = 0.98 | |
| Grossmt (Gross Movement) | |
| 1. Place hand behind head (If score = 3, total = 9 and finish) | |
| 2. (If score = 0, total = 0 and finish | |
| 3. Place hand on top of head | |
| 4. Hand to mouth | |
| Coefficient of reproducibility = 0.98 | |
| Coefficient of scalability = 0.97 | |

The Action Research Arm Test is ordered so that if the patient passes the first task in a subtest, no more tasks need to be administered and the patient scores top marks for that subtest. If the patient fails the first task and fails the second task, the patient scores zero, and again no more tests need to be performed in that subtest. Otherwise, the patient is instructed to complete all tasks within the subtest.

The illustrated patient programmer 36 also includes a patient authentication interface such as a fingerprint identification pad 43 to verify that the individual performing tasks, answering questions, and/or otherwise using the patient programmer 36 is in fact the patient. Such a solution is particularly advantageous in closed loop situations wherein real-time modification of simulation signal parameters may be possible. Other biometric authentication solutions such as retinal scans and hair follicle analysis may also be used. To further address safety concerns, the patient programmer 36 may require the patient programmer 36 and the pulse generator to be maintained in proximity to one another, as well as the maintenance of constant communication between the patient programmer 36 and the pulse generator while patient progress input is being obtained.

Figure 3B:
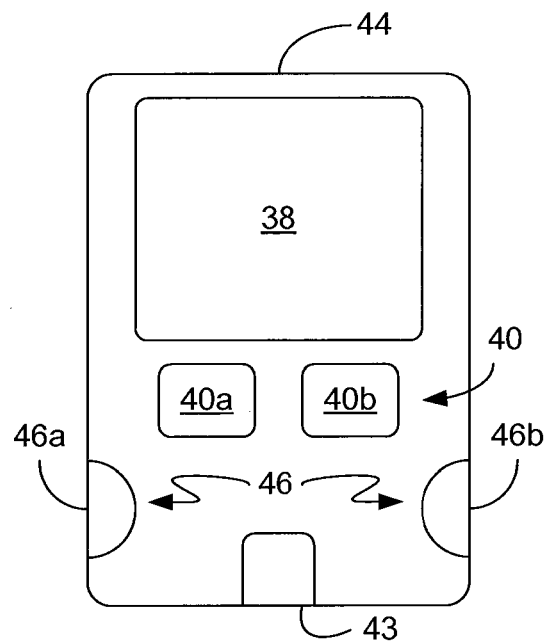
FIG. 3B is a front view of an example of a patient programmer having a plurality of pressure sensors according to an embodiment of the invention.

FIG. 3B shows an alternative design of a patient programmer 44. In the illustrated example, the patient programmer 44 has a display 38, a plurality of buttons 40 and a plurality of force transducers/pressure sensors 46 (46a, 46b), which may be squeezed by the patient to determine, for example, the patient's hand strength before, during, and/or after delivery of stimulation pulses to a desired treatment site within the patient's body. Thus, the patient programmer 44 may use the display 38 to instruct the patient to squeeze the pressure sensors 46 for a certain amount of time, wherein the pressure sensors 46 measure the amount of pressure applied by the patient. This progress input may be registered and time stamped by a processor 26 and/or progress module 22 (FIG. 1), and stored to a memory location within the patient programmer 44.

Figure 4:
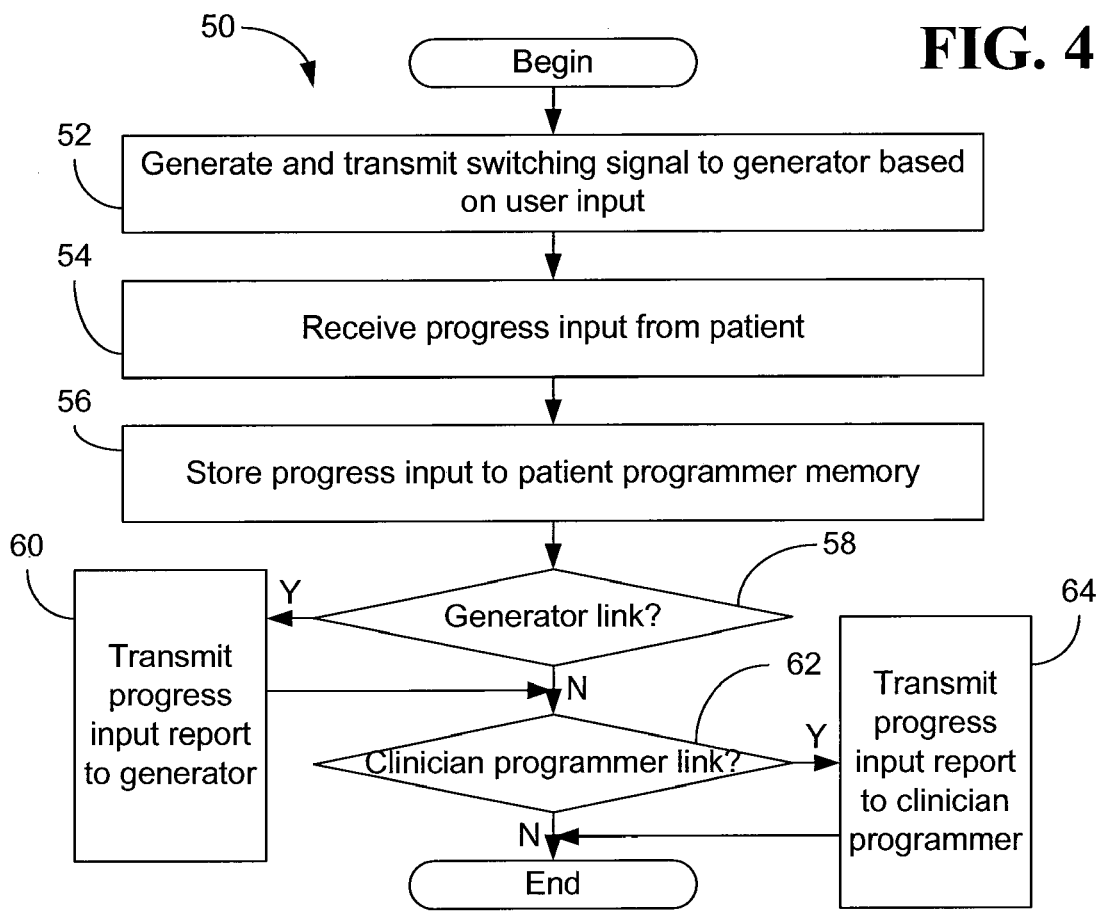
FIG. 4 is a flowchart of an example of a method of operating a patient programmer according to an embodiment of the invention.

Turning now to FIG. 4, a method 50 of operating a patient programmer is shown. The method 50 may be implemented in a patient programmer as a set of processor-executable instructions stored in ROM, RAM, electrically erasable programmable ROM (EEPROM), flash memory, etc., as fixed functionality hardware such as an embedded microcontroller, application specific integrated circuit (ASIC), etc. using complementary metal oxide semiconductor (CMOS) technology or transistor-transistor-logic (TTL), or any combination thereof. In the illustrated processing block 52, a switching signal is generated and transmitted to a generator of a stimulation signal, wherein the switching signal instructs the generator to transition between an on state and an off state. Thus, in the illustrated example, the patient programmer is able to power the generator on and off. Block 54 provides for receiving progress input from the patient and block 56 provides for storing the progress input to a memory location on the patient programmer.

If a link, such as a short range wireless link, to the generator is detected at block 58, report data representing the progress input is transmitted to the generator at block 60. Block 62 provides for determining whether a link to a clinician programmer exists and, if so, report data representing the progress input is transmitted to the clinician programmer at block 64. Once the report data is uploaded to the clinician programmer, the data may be analyzed and displayed graphically, and sorted by specific task and/or date. Graphical display of the data could be used to show trends in improvement levels and gauge the amount of patient recovery, and may lead the medical professional to a change in the stimulation parameters.

Figure 5A:
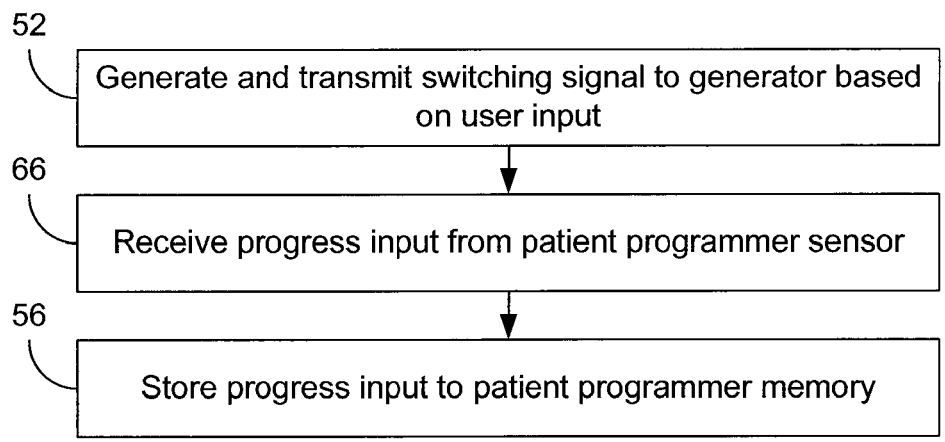
FIG. 5A is a flowchart of an example of a process of obtaining progress input from a sensor according to an embodiment of the invention.

FIG. 5A shows one approach to receiving progress input from the patient at block 66, in which the progress input is obtained from a sensor of the patient programmer. As already discussed, the sensor may be a wide variety of sensors such as pressure sensors, temperature sensors, motion/acceleration sensors, heart rate sensors, EEG sensors, strain gauges, and so on.

Figure 5B:
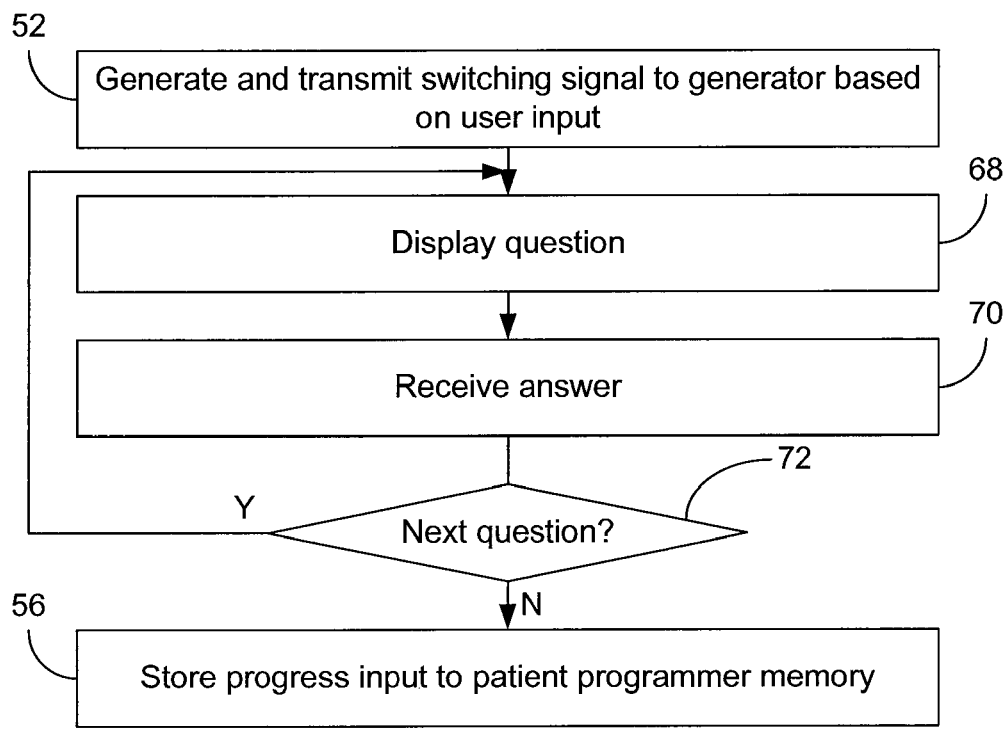
FIG. 5B is a flowchart of an example of a process of obtaining answers that define progress input according to an embodiment of the invention.

FIG. 5B shows an approach to receiving progress input from the patient, wherein a question is displayed to the patient at block 68. As already discussed, the question could be related to the patient's perception of improvement, the patient's psychological state, objective yes/no issues, or anything else regarding the patient's well-being or state of recovery. Block 70 provides for receiving an answer to the displayed question and block 72 provides for determining whether there are any remaining questions. If so, the illustrated process steps through the questions until the last question is completed.

The present invention also provides methods of monitoring the progress of a patient who has been treated with neuromodulation using a patient programmer as described herein. Such a patient programmer can be used to monitor the progress of various different types of patients including those receiving neuromodulation for treatment of stroke, traumatic brain injury, or other conditions.

The terms "connected", "coupled" and "attached" are used herein to refer to any type of relationship, direct or indirect, between the components in question, and may apply to electrical, mechanical, RF, optical or other couplings, unless otherwise indicated. In addition, the term "first", "second", and so on are used herein only to facilitate discussion, and do not necessarily infer any type of temporal or chronological relationship.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specifications, and following claims.

What is claimed is:

1. A deep brain stimulation system comprising:
a neuro-stimulation generator configured to deliver electrical energy to the patient's brain;
at least one sensor selected from the group consisting of: a force sensor, a temperature sensor, a motion/acceleration sensor, a strain gauge, and a chemical sensor; and
a patient programmer to which the at least one sensor is mounted, the patient programmer comprising:
a wireless interface configured to transmit a control signal to the generator;
a processor configured to:
generate the control signal; and
obtain from the at least one sensor, and store in a memory location, measurements characterizing one or more aspects of a particular task performed by a patient with the patient programmer; and
a communication interface to transmit report data representing the measurements to a clinician programmer.

2. The deep brain stimulation system of claim 1, further comprising a display to present a plurality of questions to the patient, and an input device to receive answers to the plurality of questions from the patient, wherein the plurality of questions include at least one of quality of life questions, object recognition questions, diary questions and cognitive questions.

3. The deep brain stimulation system of claim 2, wherein the input device includes at least one of a touch-screen component of the display and a plurality of buttons.

4. The deep brain stimulation system of claim 1, wherein the wireless interface includes at least one of a Wireless Personal Area Network (WPAN), a Bluetooth module, a Wireless Fidelity (WiFi) module and a radio frequency (RF) module.

5. The deep brain stimulation system of claim 1, wherein the communication interface includes at least one of a short range wireless interface, a long range wireless interface and a wired interface.

6. The deep brain stimulation system of claim 1, wherein the patient programmer further comprises a heart rate sensor link to receive measurement signals from a heart rate sensor coupled to the patient or an EEG sensor link to receive measurement signals from EEG sensors coupled to the patient.

7. The deep brain stimulation system of claim 1, further comprising a clinician programmer to provide stimulation parameters to the generator.

8. The deep brain stimulation system of claim 1, wherein the control signal transmitted from the patient programmer to the neuro-stimulation generator is limited to instructing the neuro-stimulation generator to turn on or off.

9. The deep brain stimulation system of claim 1, wherein the patient programmer is not adapted to adjust stimulation parameters of the neuro-stimulation generator.

10. The deep brain stimulation system of claim 1, wherein the at least one sensor is a plurality of sensors.

11. A patient programmer comprising:
at least one sensor selected from the group consisting of: a force sensor, a temperature sensor, a motion/acceleration sensor, a strain gauge, and a chemical sensor;
a communication interface configured to transmit a control signal to a generator of a stimulation signal; and
a processor configured to:
generate the control signal; and
obtain from the at least one sensor measurements characterizing one or more aspects of a particular task performed by the patient with the patient programmer.

12. The patient programmer of claim 11, wherein the at least one sensor includes a force sensor or a motion/acceleration sensor.

13. The patient programmer of claim 11, further comprising:
a display to present a plurality of questions to the patient; and
an input device to receive answers to the plurality of questions.

14. The patient programmer of claim 13, wherein the input device includes at least one of a touch-screen component of the display and a plurality of buttons.

15. The patient programmer of claim 13, wherein the plurality of questions include questions from at least one of a Barthel Index, a Short Form 36 (SF-36) Health Survey, an Action Research Arm Test and a Stroke Specific Quality of Life Scale (SS-QOL).

16. The patient programmer of claim 11, further including a memory location to store the measurements.

17. The patient programmer of claim 16, wherein the communication interface includes a wireless interface configured to transmit report data representing the measurements to a generator.

18. The patient programmer of claim 11, further including an authentication interface to verify that an individual using the patient programmer is the patient.

19. A method of operating the deep brain stimulation system of claim 1 comprising:
generating, by the processor, the control signal;
transmitting the control signal from the patient programmer to the neuro-stimulation generator, the control signal instructing the neuro-stimulation generator to transition between an on state and an off state; and
obtaining, by the processor, input from the at least one sensor.

20. The method of claim 19, further comprising:
obtaining input by displaying a plurality of questions to the patient and receiving answers to the plurality of questions.

21. The method of claim 19, further including storing the input to the memory location on the patient programmer.

22. The method of claim 19, further including transmitting report data representing the input to the generator.

23. The method of claim 19, further including transmitting report data representing the input to a clinician programmer.

* * * * *